United States Patent [19]

Kawamura et al.

[11] Patent Number: 4,886,756

[45] Date of Patent: Dec. 12, 1989

[54] NOVEL RESTRICTION ENDONUCLEASE SPLI AND PROCESS FOR THE PRODUCTION OF THE SAME

[75] Inventors: Masahide Kawamura; Masaki Sakakibara; Teruo Watanabe, all of Chiba; Akira Obauashi, Uji; Nobutsugu Hiraoka, Mukou; Keiko Kita, Kyoto, all of Japan

[73] Assignees: Dainippon Ink and Chemicals, Inc., Tokyo; Takara Shuzo Co., Ltd., Kyoto, both of Japan

[21] Appl. No.: 758,536

[22] Filed: Jul. 24, 1985

[30] Foreign Application Priority Data

Aug. 2, 1984 [JP] Japan .................. 59-161609

[51] Int. Cl.$^4$ .................. C12N 9/22; C12N 9/00; C12N 9/14
[52] U.S. Cl. .................. 435/199; 435/183; 435/195; 935/77; 935/82
[58] Field of Search .............. 435/183, 195, 199, 946; 935/77, 82

[56] References Cited

PUBLICATIONS

Boehringer Mannheim Poster, 1982.
Shinomiya, T., et al., "A Second Site Specific Endonuclease from Thermus Thermophilus 111, Tth 111 III", *Nucleic Acids Research*, 8, (15), (1980), 3275–3285.

*Primary Examiner*—Charles F. Warren
*Assistant Examiner*—Gail F. Knox

*Attorney, Agent, or Firm*—Browdy and Neimark

[57] ABSTRACT

A novel restriction endonuclease SpII which has the following physicochemical properties:
(1) recognizing the following base sequences in double-stranded deoxyribonucleic acid

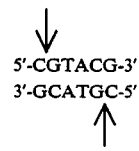

and cleaving said sequences in the phosphodiester bonds between C and G as indicated with the vertical arrows to produce DNA fragments having one strand comprising four bases at the 5'-terminal;
(2) cleaving double-stranded deoxyribonucleic acid λ-DNA in one position, Col El in two positions and φx 174 RF in two positions;
(3) being activated with 5 to 20 mM $Mg^{2+}$; and
(4) exhibiting an activity at a NaCl concentration of 0 to 200 mM;

and a process for the production of the restriction endonuclease SpII which comprises culturing a restriction endonuclease SpII-producing alga belonging to the genus *Spirulina*, collecting the cells, obtaining a cell-free extract therefrom the separating and purifying the restriction endonuclease SpII.

2 Claims, No Drawings

NOVEL RESTRICTION ENDONUCLEASE SPLI AND PROCESS FOR THE PRODUCTION OF THE SAME

BACKGROUND OF THE INVENTION

Field of the Invention

This invention relates to a novel restriction endonuclease SpII and a process for the production of the same.

A restriction endonuclease is generally a deoxyribonuclease which recognizes several specific base sequences in double-stranded deoxyribonucleic acid (hereinafter referred to as DNA) molecules and cleaves the strands. These restriction endonucleases are useful in studying the structure and function of DNA since they can cleave the strands of a long DNA molecule at specific sites to produce DNA fragments which may be subjected to base sequence analysis. Furthermore they are essential as reagents which are extremely valuable in genetic engineering.

We have studies on a restriction endonuclease, which is extremely valuable in the art as a biochemical reagent as described above, originating from algae which have not been sufficiently studied.

SUMMARY OF THE INVENTION

We have found that algae belonging to the genus *Spirulina* produce an unknown restriction endonuclease SpII which specifically cleaves DNA, thus completing the present invention.

The novel restriction endonuclease SpII of the present invention has the following physicochemical properties.

(1) Recognizing the following base sequence in double-stranded deoxyribonucleic acid:

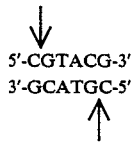

```
5'-CGTACG-3'
3'-GCATGC-5'
``` and cleaving said sequences in the phosphodiester bonds between C and G as indicated-with the vertical arrows to produce DNA fragments having a single strand comprising four bases at the 5'-terminal.

(2) Cleaving double-stranded deoxyribonucleic acid λ-DNA in one position, Col El in two positions and φX 174 RF in two positions.

(3) Being activated with 5 to 20 mM $Mg^{2+}$.

(4) Exhibiting an activity at a NaCl concentration of 0 to 200 mM.

The present invention further relates to a process for the production of the novel restriction endonuclease SpII which comprises culturing a restriction endonuclease SpII-producing alga belonging to the genus *Spirulina*, collecting the cells, obtaining a cell-free extract therefrom and separating and collecting the restriction endonuclease SpII from the cell-free extract.

DETAILED DESCRIPTION OF THE INVENTION

The positions in which the restriction endonuclease SpII of the present invention cleaves φX 174 RF DNA (mfd. by Takara Shuzo Co., Ltd.) was determined by double-digesting said φX 174 RF DNA with the restriction endonuclease of the present invention and a restriction endonuclease of well known properties. As a result, it was concluded that the restriction endonuclease of the present invention would cleave the φX 174 RF DNA in Nos. 430±20 and 2810±20 positions each assigned by referring to the position cleaved by Pst I as No. 0. λ DNA was also subjected to the same procedure and consequently it was found that the restriction endonuclease of the present invention would cleave said λ DNA in No. 19,000 ±500 position. It was further found that the restriction endonuclease of the present invention would not cleave pBR 322 nor pA03These facts and a computerized examination by C. Fuchs et al. (see Gene, vol. 10, 357–370, 1980) suggest that the nucleotide sequence on DNA recognized by the restriction endonuclease of the present invention is CGTACG. The cleaved site on recognition sequence of the endonuclease of the present invention was further determined by analyzing the terminal base sequence of the two fragments obtained by cleaving φX 174 RF DNA with the endonuclease of the present invention according to the Maxam-Gilbert's method (see Proc. Natl. Acad. Sci. USA, vol. 74, 560, 1977).

Now the above mentioned method will be described in detail.

φX 174 RF DNA (mfd. by Takara Shuzo Co., Ltd.) was completely decomposed with the endonuclease of the present invention and treated with alkaline phosphatase (mfd. by Sigma) to thereby remove the terminal phosphate of a DNA fragment Subsequently a radioactive phosphate was added to the 5'-terminal of the DNA fragment with the use of polynucleotide kinase (mfd. by Takara Shuzo Co., Ltd.) and [γ-$^{32}$P]adenosine triphosphate to give a DNA fragment having $^{32}$P-phosphate at each terminal, which was then cleaved with Tth HB 8I (mfd. by Takara Shuzo Co., Ltd.) and subjected to 5 % acrylamide gel electrophoresis to obtain a fragment labelled with $^{32}$P at only one terminal. Among four radioactive bands detected in the electrophoresis, those of 65 bp and 250 bp in length were separately extracted and the 5'-terminal of each band was analyzed according to the Maxam-Gilbert's method as described above. Consequently it was found that the base sequence in the vicinity of the cleaved position is as follows:

-5'-GTACGTTTCCA—

—GCATG—5'-

The above result suggests that the enzyme of the present invention recognizes

5'-CGTACG—3'

3'-GCATGC—5' and forms a cleaved positon of

5'-C—3'5'-GTACG—3'

3'-GCATG—5'3'-C—5'.

The cleaved position as examined herein is φX 174 RF DNA No. 414 and well concides with the cleaved site No. 430±20 as described above.

Thus the cleaved position recognizing site of the endonuclease of the present invention is as follows:

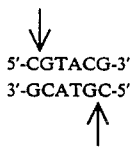

```
5'-CGTACG-3'
3'-GCATGC-5'
``` wherein the cleaved position is indicated with the vertical arrows. The endonuclease of the present invention is named SpII according to the Smith-Nathans' Nomenclature (see J. Mol. Biol., vol. 81, 419–423, 1973).

The restriction endonuclease SpII, which is a novel restriction endonuclease since the substrate specificity thereof can not be found in the list of restriction endonucleases by Richard J. Roberts (see Nucleic Acids Research, vol. 12, γ 167, 1984), has the following properties.

(1) Substrate specificity

Table 1 shows the number of the positions in which the endonuclease of the present invention cleaves various substrate DNA.

TABLE 1

| substrate DNA | Number of cleaved positions |
| --- | --- |
| λ DNA | 1 |
| Col El | 2 |
| pBR 322 | 0 |
| φX 174 RF | 2 |

The endonuclease recognizes the following base sequence:

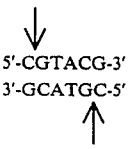

```
5'-CGTACG-3'
3'-GCATGC-5'
``` and cleaves said sequence in the phosphodiester bonds between C and G to produce DNA fragments having a single strand comprising four bases at the 5'-terminal.

(2) NaCl concentration

The endonuclease exhibits an activity at a NaCl concentration of 0 to 200 mM and the maximum activity at 100 to 120 mM when determined by employing solutions adjusted to a NaCl concentration of 0 to 200 mM and treating in the same manner as that of the measurement of its titer as will be described hereinbelow.

(3) Optimum pH

The endonuclease exhibits an activity in a range of pH 5.5 to 10.0 and the maximum activity in a range of pH 7.0 to 7.5, when determined by employing solutions adjusted to pH 3.5 to 5.5, to pH 5.5 to 7.5, to pH 7.2 to 9.0 and to pH 8.6 to 11 with acetate, with Tris malate/sodium hydroxide, with Tris hydrochloride and with glycine/sodium hydroxide, respectively, and treating in the same manner as that of the measurement of its titer as will be described hereinbelow.

(4) Optimum reaction temperature

The endonuclease exhibits an activity in a temperature range of 20° to 65° C. and it is found that the optimum reaction temperature thereof is 50° to 55° C., when determined in the same manner as that of the measurement of its titer as will be described hereinbelow except that the reaction temperature is varied from 20° to 75° C.

(5) Inactivation (temperature stability)

A test solution of the endonuclease is adjusted to a pH value of 7.5 and treated in the same manner as that of the measurement of its titer as will be described hereinbelow. As a result, the enzyme of the present invention is completely inactivated at 75° C.

(6) Measurement of titer

The endonuclease is added to a solution containing a 10 mM of Tris hydrochloride buffer (pH 7.5), 7 mM of $MgCl_2$, 7 mM of 2-mercaptoethanol, 100 mM of NaCl, 0.01% of bovine serum albumin and various bacteriophage DNA or plasmid DNA and the obtained mixture is allowed to react at 55° C. for 60 min. The reaction products are subjected to 0.7 % agarose gel elecreophoresis and the resulting agarose plates are irradiated with ultraviolet rays in the presence of ethidium bromide. Fluorescence thus irradiated is photographed to thereby detect the electrophoretic pattern as bands. The number of the bands and positions and amounts of each band are measured.

(7) Activation

The endonuclease is activated with 5 to 20 mM of $Mg^{2+}$ without requiring any cofactor such as ATP or S-adenosylmethionine.

(8) Molecular weight r weight of the endonuclease determined by gel-filtration with the use of Sephadex G150 (mfd. by Pharmacia Fine Chemicals) is approximately 400,000±30,000.

Examples of the restriction endonuclease SpII-producing algae as described above are some known strains including Spirulina platensis M-185 (ATCC 53844) and Spirulina maxima UTEX LB-2342 (ATCC 53871) and Spirulina platensis subsp. siamese (ATCC 53843) which has been isolated from a saline lake in Ethiopia by us. S. platensis M-185 is a known strain which is deposited with the Institute of Applied Microbiology, the University of Tokyo, as a systematic microalgae culture collection, while S. maxima UTEX LB-2342 is a known strain which is deposited with the Culture Collection of Algae, the University of Texas, Austin.

Spirulina may be cultured in a conventional manner. It is preferable to culture it in a medium containing sodium bicarbonate as a main component and to maintain the medium at pH 8 to 9.5 during the incubation.

After the completion of the incubation, the culture broth is filtered to collect the cells on paper or cloth filters. The endonuclease may be extracted and purified according to a conventional manner. For example, the obtained cells are suspended in a buffer solution, ultrasonically disrupted and centrifuged to give a cell-free extract. The extract is treated with 5 to 10 % by weight of streptomycin sulfate or polyethyleneimine, fractionated with ammonium sulfate and purified by ion exchange chromatography with the use of phosphocellulose or DEAE-cellulose, affinity chromatography with the use of heparin agarose or DNA-cellulose or a combination of these methods to give the aimed endonuclease Thus the present invention successfully provides a novel restriction endonuclease by using Spirulina which is readily cultured and from which the aimed endonuclease is readily extracted, to thereby significantly contribute various studies and arts in the field of biochemistry, genetic engineering and the like wherein restriction endonucleases are required.

These SpII-producing algae belonging to the genus of *Spirulina* frequently have other restriction endonucleases such as isoschizomers of Tth 111I, HaeIII, PvuI and PvuII. For example, the presence of two restriction endonucleases named SplII and SplIII other than SplI is confirmed in S. platensis. SplII is an isoschizomer of Tth111I produced by *Thermus thermophilus* 111 strain while SplIII is an isoschizomer of HaeIII produced by *Haemophilus aegyptius* ATCC-11116 strain. On the other hand, *S. maxima* has three restriction endonucleases named SmxII, SmxIII and SmxIV other than SpII which is also called SmadI or SmxI. SmxII is an isoschizomer of Tth111I produced by *T. thermophilus* 111 strain, SmxIII is an isoschizomer of PvuI produced by *Proteus vulgaris* and SmxIV is an isoschizomer of PvuII produced by *P. vulgaris*.

These restriction endonucleases other than SpII can be successively or simultaneously isolated during the extraction and isolation of SpII. It is preferable that the supernatant of the cell-free extract obtained by removing DNA is fractionated with ammonium sulfate and separated by ion exchange chromatography with the use of DEAE-cellulose or the like followed by purification by the above ion exchange chromatography, affinity chromatography or a combination of these methods.

To further illustrate the present invention, the following Examples will be given wherein percentage is given by weight.

EXAMPLE 1

*S. platensis* M-185 was inoculated on the SOT medium as shown in Table 2 to give an OD of 0.1 at 560 nm and cultured therein at 35° C. with shaking under illuminating at 7000 lux. The turbidity thereof determined after seven days was OD 1.5 at 560 nm. 50 l of the resulting culture solution was filtered with a 500-mesh cloth filter to give approximately 100 g of cells on wet basis.

TABLE 2

| Composition of SOT medium | |
|---|---|
| NaHCO$_3$ | 16.8 g/l |
| K$_2$HPO$_4$ | 0.5 g/l |
| NaNO$_3$ | 2.5 g/l |
| K$_2$SO$_4$ | 1.0 g/l |
| NaCl | 7.0 g/l |
| MgSO$_4$.7H$_2$O | 0.2 g/l |
| CaCl$_2$.7H$_2$O | 0.04 g/l |
| FeSO$_4$.7H$_2$O | 0.01 g/l |
| EDTA | 0.08 g/l |
| Solution A$_5$ | 1 ml/l |
| Solution A$_5$ | |
| H$_3$BO$_3$ | 2.85 g/l |
| MnCl$_2$.4H$_2$O | 1.81 g/l |
| ZnSO$_4$.7H$_2$O | 0.22 g/l |
| CuSO$_4$.5H$_2$O | 0.08 g/l |
| MoO$_3$ | 0.015 g/l |

In order to determine the activity of the restriction endonuclease SpII, the endonuclease was added to a solution containing 1 µg of Col El as substrate DNA, 10 mM of Tris hydrochloride, 7 mM of MgCl$_2$, 7 mM of 2-mercaptoethanol and 100 mM of NaCl (pH 7.5) to give a total volume of 50 µl and the obtained mixture was allowed to react at 55° C. for one hour. The resulting products were analyzed by agarose electrophoresis. The enzymatic activity required to completely digest 1 µg of DNA under the above condition was defined as one unit.

The obtained wet cells were suspended in the buffer A containing 10 mM of potassium phosphate buffer (pH 7.4), 7 mM of 2-mercaptoethanol and 1 mM of EDTA in a volume three times as much as the cells, ultrasonically disrupted and centrifuged at 10,000 × g for one hour to remove cell debris, thus giving a cell-free extract. To the extract, an aqueous solution of streptomycin sulfate (5 to 10 %) was added to give a final concentration of 2 %. The mixture was stirred for 30 min and centrifuged at 15,000 × g for 20 min to remove the endogenous DNA, and RNA thus giving the supernatant. Ammonium sulfate was added to the supernatant to give a 70 % saturated solution and the precipitate thus formed was collected by centrifuging at 15,000 × g for 20 min. The collected precipitate was dissolved in the buffer B containing 10 mM of Tris hydrochloride (pH 7.3), 7mM of 2-mercaptoethanol, 1 mM of EDTA and 10 % (v/v) of glycerol and dialyzed against the same buffer overnight. The dialyzed solution was adsorbed by a DEAE-cellulose column (Watman DE 52; 2.5×30 cm) previously equilibrated with the buffer B, washed with the buffer B and eluted with the buffer B of 0 to 0.5 M linear gradient of NaCl. Consequently the fraction of 0.05 to 0.2 M of NaCl exhibited the activity.

The resulting fraction was dialyzed against the buffer C containing the buffer A containing 10 % of glycerol overnight, adsorbed by a SP Sephadex column (mfd. by Pharmacia Fine Chemicals; 3.0×30 cm), washed with the buffer C and eluted with the buffer C of 0 to 0.6 M linear gradient of NaCl. Consequently the fraction of 0.2 to 0.5 M NaCl exhibited the activity. The active fraction was dialyzed against the buffer B overnight, adsorbed by a DEAE-cellulose column (1.2×15 cm), washed with the buffer B and eluted with the buffer B of 0 to 0.5 M linear gradient of NaCl. Consequently the fraction of 0.05 to 0.2 M NaCl exhibited the activity of the restriction endonuclease SpII to give an active fraction of approximately 5,000 unit.

EXAMPLE 2

*S. Maxima* UTEX LB-2342 was cultured in the same manner as described in Example 1 to give approximately 110 g of wet cells. The restriction endonuclease was purified in the same manner as described in Example 1. As a result, an active fraction of SpII of approximately 8,000 unit was obtained.

EXAMPLE 3

Active fractions of restriction enzymes other than SpLI obtained from the cell-free extract of *S. platensis* M-185 as described in Example 1 were purified in the same manner as described in Example 1 with the use of DEAE-cellulose (Watman DE 52), SP sephadex (mfd. by Pharmacia Fine Chemicals) and DEAE-cellulose columns to give two restriction endonucleases, i.e. SplII and SplIII. SplII (approximately 3,000 unit) was an isoschizomer of Tth 111I while SplIII (approximately 4,500 unit) was an isoschizomer of Hae III.

Approximately 6,000 unit of SpII was further obtained in the same manner as described in Example I.

We claim:

1. An essentially pure restriction endonuclease SPII which has the following physicochemical properties:

(1) recognizing the following base sequence in double-stranded deoxyribonucleic acid molecules:

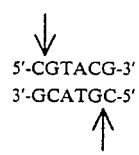

5'-CGTACG-3'
3'-GCATGC-5' and cleaving said sequence in the phosphodiester bonds between C and G as indicated with the vertical arrows to produce DNA-fragments having one strand comprising four bases at the 5'-terminal;
(2) cleaving double-stranded deoxyribonucleic acid λ-DNA in one position, COl El in two positionss and φX 174 in two positions;
(3) being activated with 5 to 20 mM $Mg^{2+}$;
(4) exhibiting an activity at a NaCl concentration of 0 to 200 mM and having an optimum NaCl concentration of 100 to 120 mM;
(5) having a working pH value of 5.5 to 10.0 and an optimum pH value of 7.0 to 7.5;
(6) having a working temperature of 20° to 65° C. and an optimum temperature of 50° to 55° C.;
(7) being completely inactivated ast 75° C. for 60 min (i.e. temperature stability);
(8) having a molecular weight of approximately 400,000±30,000 when determined by a gel-filtration method; and
(9) being activated 5 to 20 mM $Mg^{2+}$ without requiring ATP or S-adenosyl-methionine as confactors; and which can be produced by culturing *Spirulinas platensis* subspecies *siamese* (ATCC 53843) or M-185 (ATCC 53844), or *Spirulina maxima* UTEX LB-2342 (ATCC 53871) and purifying an endonuclease having said physicochemical properties from said culture.

2. An essentially pure restriction endonuclease SplI which has the following physicochemical properties:
(1) recognizing the following base sequences in double-stranded deoxyribonucleic acid molecules:

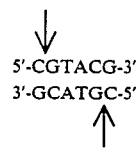

5'-CGTACG-3'
3'-GCATGC-5' and cleaving said sequences in the phosphodiester bonds between C and G as indicated with the vertical arrows to produce DNA-fragments having one strand comprising four base at the 5'-terminal;
(2) cleaving double-stranded deoxyribonucleic acid λ-DNA in one position, Col El in two positions and φX 174 RF in two positions;
(3) being activated with 5 to 20 mM $Mg^{2+}$;
(4) exhibiting an activity at a NaCl concentration of 0 to 200 mM and having an optimum NaCl concentration of 100 to 120 mM;
(5) having a working pH value of 5.5 to 10.0 and an optimum pH value of 7.0 to 7.5;
(6) having a working temperature of 20 to 65° C. and an optimum temperature of 50° 55° C.;
(7) being completely inactivated at 75° C. for 60 min (i.e. temperature stability);
(8) having a molecular weight of approximately 400,000±30,000 when determined by a gel-filtration method; and
(9) being activated with 5 to 20 mM $Mg^{2+}$ without requiring ATP or S-adenosyl-methionine as cofactors; and which is purified from a culture of *Spirulina plantensis* subspecies *siamese* (ATCC 53843) or M-185 (ATCC 53844), or *Spirulina maxima* UTEX LB-2342 (ATCC 53871).

* * * * *